United States Patent [19]

Ryan et al.

[11] Patent Number: 4,707,490
[45] Date of Patent: * Nov. 17, 1987

[54] ANTI-HYPERTENSIVE AGENTS

[75] Inventors: James W. Ryan; Alfred Chung, both of Miami, Fla.

[73] Assignee: University of Miami, Miami, Fla.

[*] Notice: The portion of the term of this patent subsequent to Sep. 1, 2004 has been disclaimed.

[21] Appl. No.: 850,055

[22] Filed: Apr. 10, 1986

Related U.S. Application Data

[63] Continuation of Ser. No. 680,541, Dec. 11, 1984, abandoned, which is a continuation of Ser. No. 524,204, Aug. 18, 1983, abandoned, which is a continuation of Ser. No. 295,589, Aug. 24, 1981, abandoned, which is a continuation of Ser. No. 116,951, Jan. 30, 1980, abandoned, which is a continuation of Ser. No. 958,180, Nov. 6, 1978, abandoned.

[51] Int. Cl.$^4$ .................. A61K 31/40; C07D 207/244; C07C 101/72
[52] U.S. Cl. .................. 514/423; 548/533; 562/445
[58] Field of Search .................. 548/533; 514/423; 562/445

[56] References Cited

U.S. PATENT DOCUMENTS

| | | | |
|---|---|---|---|
| 3,023,235 | 2/1962 | Leonard | 562/445 |
| 3,725,470 | 4/1973 | Bretschneider et al. | 562/445 |
| 4,046,889 | 9/1977 | Ondetti et al. | 548/533 |
| 4,053,651 | 10/1977 | Ondetti et al. | 514/562 |
| 4,105,776 | 8/1978 | Ondetti et al. | 548/533 |
| 4,241,076 | 12/1980 | Ondetti et al. | 548/533 |

Primary Examiner—Delbert R. Phillips
Attorney, Agent, or Firm—Mary Helen Sears

[57] ABSTRACT

ACE inhibitors containing amino acid esters of thiopropanoyl-L-3,4-dehydroproline are disclosed.

13 Claims, No Drawings

ANTI-HYPERTENSIVE AGENTS

PARENT APPLICATIONS

The present application is a continuation of our application Ser. No. 680,541, filed Dec. 11, 1984 and now abandoned, which was a continuation of our application Ser. No. 524,204, filed Aug. 18, 1983 and now abandoned, which was a continuation of our application Ser. No. 295,589, filed Aug. 24, 1981 and now abandoned, which was a continuation of our application Ser. No. 116,951, filed Jan. 30, 1980, and now abandoned, which was a continuation of our application Ser. No. 958,180, filed Nov. 6, 1978, and also now abandoned.

BACKGROUND OF THE INVENTION

Angiotensin converting enzyme (peptidyldipeptide hydrolase, hereinafter referred to as ACE) occupies a central role in the physiology of hypertension. The enzyme is capable of converting the decapeptide angiotensin I, having the sequence AspArgValTyrIleHisProPheHisLeu to an octapeptide, angiotensin II by removal of the carboxyterminal HisLeu. The symbols for various chemical entities are explained in the following table:
Ala=L-alanine
Arg=L-arginine
Asp=L-aspartic acid
<Glu=pyro-L-glutamic acid
Gly=glycine
Hip=Hippuric acid (Benzoyl glycine)
His=L-histidine
Ile=L-isoleucine
Leu=L-leucine
Phe=L-phenylalanine
Pro=L-proline
ΔPro=L-3,4-dehydroproline
Ser=L-serine
Trp=L-tryptophan
Tyr=L-tyrosine
Val=L-valine
ACE=Angiotensin converting enzyme
Hepes=N-2-hydroxyethylpiperazine-N'-2-ethanesulfonic acid Angiotensin I is formed by the action of the enzyme renin, an endopeptidase found in kidney, other tissues and plasma, acting on a serum α-2 globulin.

Blood pressure is affected by certain peptides found in the blood. One of these, angiotensin II, is a powerful pressor (blood pressure elevating) agent. Another, bradykinin, a nonapeptide with the sequence ArgProProGlyPheSerProPheArg is a powerful depressor (blood pressure lowering) agent. In addition to a direct pressor effect, angiotensin II stimulates release of aldosterone which tends to elevate blood pressure by causing retention of extracellular salt and fluids. Angiotensin II is found in measurable amount in the blood of normal humans. However, it is found at elevated concentrations in the blood of patients with renal hypertension.

The level of ACE activity is ordinarily in excess, in both normal and hypertensive humans, of the amount needed to maintain observed levels of angiotensin II. However, it has been found that significant blood pressure lowering is achieved in hypertensive patients by treatment with ACE inhibitors. Gavras, I., and Vukovich, R. A., *New Engl. J. Med.* 291, 817 (1974)].

ACE is a peptidyldipeptide hydrolase. It catalyzes the hydrolysis of the penultimate peptide bond at the C-terminal end of a variety of acylated tripeptides and larger polypeptides having an unblocked α-carboxyl group. The action of ACE results in hydrolytic cleavage of the penultimate peptide bond from the carboxyl-terminal end yielding as reaction products a dipeptide and a remnant.

The reactivity of the enzyme varies markedly depending on the substrate. At least one type of peptide bond, having the nitrogen supplied by proline, is not hydrolyzed at all. The apparent Michaelis constant ($K_m$) varies from substrate to substrate over several orders of magnitude. For general discussion of the kinetic parameters of enzyme catalyzed reactions, see Lehninger, A., *Biochemistry*, Worth Publishers, Inc., New York, 1970, pp. 153–157. Many peptides which are called inhibitors of the enzymatic conversion of angiotensin I to angiotensin II are in fact substrates having a lower $K_m$ than angiotensin I. Such peptides are more properly termed competitive substrates. Examples of competitive substrates include bradykinin, and the peptide $BPP_{5a}$ (also called SQ20475) from snake venom, whose sequence is <GluLysTrpAlaPro.

Numerous synthetic peptide derivatives have been shown to be ACE inhibitors by Ondetti, et al. in U.S. Pat. No. 3,832,337 issued Aug. 27, 1974.

The role of ACE in the pathogenesis of hypertension has prompted a search for inhibitors of the enzyme that could act as antihypertensive drugs. See for example U.S. Pat. Nos. 3,891,616, 3,947,575, 4,052,511 and 4,053,651. A highly effective inhibitor, with high biological activity when orally administered, is D-3-mercapto-2-methylpropanoyl-L-proline, designated SQ14225, disclosed in U.S. Pat. No. 4,046,889 to Ondetti et al., issued Sept. 6, 1977, and in scientific articles by Cushman, D. W. et al., *Biochemistry* 16, 5484 (1977), and by Ondetti, M. et al., *Science* 196, 441 (1977). The inhibitor SQ14225 reportedly has an $I_{50}$ value of $2.3 \times 10^{-8}$M. The $I_{50}$ value is defined as a concentration of inhibitor required to produce 50% inhibition of the enzyme under a standard assay system containing an approximately $K_m$ lovel of substrate. It will be understood that $I_{50}$ values are directly comparable when all potential factors affecting the reaction are kept constant. These factors include the source of enzyme, its purity, the substrate used and its concentration, and the composition of the assay buffer. All $I_{50}$ data reported herein have been performed with the same assay system and same enzyme (human urinary ACE) and are therefore internally consistent. Discrepancies with data obtained by other workers may be observed. Indeed such discrepancies do exist in the literature, for unknown reasons. See, for example, the $I_{50}$ values for $BPP_{9a}$ reported by Cushman, D. W., et al., *Experientia* 29, 1032 (1973) and by Dorer, F. E., et al., *Biochim. Biophys. Acta* 429, 220 (1976).

The mode of action of SQ 14,225 has been based upon a model of the active site of ACE developed by analogy with the better known related enzyme, carboxypeptidase A. The active site was hypothesized to have a cationic site for binding the carboxyl end group of the substrate and a pocket or cleft capable of binding the side chain of the C-terminal amino acid and providing especially tight binding for the heterocyclic ring of a terminal proline residue. A similar pocket for the penultimate amino acid residue was postulated, and the published data suggested a rather stringent steric requirement, since the D-form of the inhibitor was substantially more potent than its stereoisomer or the 3-methyl and unsubstituted analogs. The sulfhydryl group on the inhibitor, postulated to be bound at the active site near the catalytic center, was believed to play a central role in inactivation of the enzyme by combining with the zinc moiety known to be essential for catalytic activity. Substituents on the sulfhydryl, such as a methyl group, and an S-acetyl derivative, substantially reduced potency of the inhibitor. See Cushman, D. W., et al., *Biochemistry, supra.*

In vitro study by the mechanism by which SQ 14,225 and its analogs act to inhibit ACE has been somewhat hampered by the instability of these molecules under ambient conditions. For example, it has been observed that a fresh aqueous solution of concentration, e.g., 1 mg per ml of SQ 14,225 at a pH of about 8 becomes substantially less active upon standing for as little as 30 minutes, and that activity continues to decrease as the solution stands for longer periods. It is believed that this loss in activity is mainly the result of dimerization of SQ 14,225 occurring at the sulfhydryl end groups, whereby a disulfide is formed which is largely inactive as an inhibitor. Since the free sulfhydryl group is highly reactive and may be readily oxidized to polar acidic moieties such as sulfone and sulfoxide groups, it may also be that the observed in vitro loss of activity of aqueous solutions of SQ 14,225 on standing is in some part a consequence of one or more such oxidation reactions, with formation of a sulfone or sulfoxide which does not function effectively as an inhibitor for ACE.

Such reports of SQ 14,225 clinical testing as are currently available, some of which refer to the compound under the name "Captopril", suggest that the product is sufficiently stable in the normal gastric and intestinal environments of most patients to be an effective inhibitor for ACE when administered orally. It is not yet clear, however, whether there may be a group of patients for which SQ 14,225 is substantially ineffective. Because of the high reactivity of the free sulfhydryl group, SQ 14,225 could readily form mixed disulfides with serum, cellular proteins, peptides or other free sulfhydryl group-containing substances in the gastric or intestinal environments, in addition to the possibility for dimer formation or oxidative degradation reactions. A mixed disulfide with protein may be antigenic and, indeed, occasional allergic reactions have been clinically observed. See Gavras, et al., *New England J. Med.* 298, 991 (1978). Disulfide and oxidative degradation products of SQ 14,225, if formed, may at best be expected to be largely ineffective as inhibitors. It may be hypothesized accordingly that dose response to SQ 14,225 may vary with conditions of administration and among individual patients. Moreover, in at least some patients, unwanted side effects may occur and maintenance of an effective concentration of the inhibitor in the body may be difficult to control.

Thiolester compounds generally are thought to be highly reactive in that the thiolester linkage is readily hydrolyzable to a sulfhydryl moiety and a carboxylic moiety. Thiolesters are accordingly often used as active ester intermediates for acylation under mild conditions. Such groups as, e.g., acetylthio have been used as blocking groups in the above cited Ondetti, et al. patents. Thiolester intermediates are also postulated to occur in the biosynthesis of cyclic peptides such as tyrocidin or gramicidin S. See Lipmann, F. in *Accounts Chem. Res.* 6, 361 (1973).

Thiolester compounds having potent ACE inhibitory activity and oral effectiveness as anti-hypertensive agents have been disclosed in U.S. application Ser. No, 941,289, filed Sept. 11, 1978, incorporated herein by reference. The previously disclosed compounds are: N-[3-(benzoylphenylalanylthio)-2-D-methylpropanoyl]-L-proline ($I_{50} \approx 1 - 4 \times 10^{-8}M$), N-(2-benzoylphenylalanylthiopropanoyl)-L-proline ($I_{50} \approx 4-7 \times 10^{-8}M$ for racemic compound) and N-(3-benzoylphenylalanylthiopropanoyl)-L-proline ($I_{50} \approx 7-10^{-7}M$). Unless noted otherwise, all amino acids are in their L-forms.

Compounds related to SQ 14,225 have been disclosed by Ondetti, et al., U.S. Pat. Nos. 4,046,889, 4,052,511, 4,053,651 and 4,113,715. Of interest are disclosed analogs of SQ 14,225 having the five-membered heterocyclic ring of proline replaced by a four- or a six-membered ring. The inhibitory potencies of such analogs relative to SQ 14,225 are not disclosed. Substitution of D-proline for L-proline is reported to drastically reduce inhibitory potency of 3-mercaptopropanoyl amino acids (Cushman, D. W., et al., supra).

SUMMARY OF THE INVENTION

Novel inhibitors of ACE are disclosed:

A.     N-[3-(benzoylphenylalanylthio)-2-D-methylpropanoyl]-L-3,4-dehydroproline,

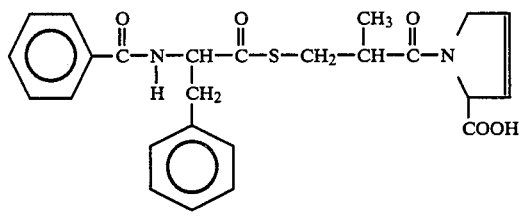

B.     N-(2-benzoylphenylalanylthiopropanoyl)-L-3,4-dehydroproline,

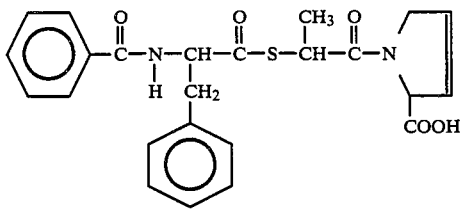

C.     N-(3-benzoylphenylalanylthiopropanoyl)-L-3,4-dehydroproline,

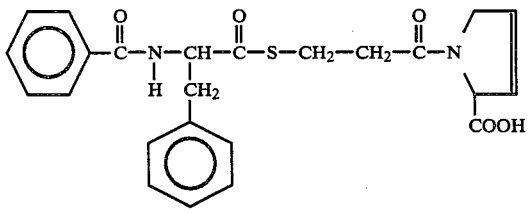

The disclosed compounds are inhibitors of ACE and are useful as orally effective anti-hypertensive agents.

DETAILED DESCRIPTION OF THE INVENTION

The discovery of ACE inhibitory potency in the compounds of the present invention provides a unique approach to the design of inhibitory compounds. Although many prior art inhibitors are proline derivatives, substitution of other amino acids for proline has also yielded potent inhibitors. Arginine, phenylalanine and alanine are all effective substituents for proline, so that a trend is not discernible.

Derivatives of bradykinin having a proline in the 2, 3 or 7 position substituted by L-3,4-dehydroproline have been studied for physiological effect on the contractile response of rat uterus and guinea pig ileum. See Fisher, G. H., et al., *Arch.Biochem.Biophys.* 189, 81 (1978). The analogs $\Delta pro^2$-bradykinin and $\Delta pro^3$-bradykinin were approximately as effective as bradykinin, while $\Delta pro^7$-bradykinin was only about 25% as effective.

On the other hand, the incorporation of L-3,4-dehydroproline in the place of proline has been found to enhance the potency of the ACE inhibitor $BPP_{9a}$. The peptides $\Delta Pro^3$-$BPP_{9a}$, $\Delta Pro^5$-$BPP_{9a}$ and $\Delta Pro^9$-$BPP_{9a}$ are substantially more potent inhibitors than $BPP_{9a}$ itself, and these compounds are effective anti-hypertensive agents when administered intravenously. The compound, $\Delta Pro^8$-$BPP_{9a}$ is ACE-inhibitory, but less potent than $BPP_{9a}$.

No clear picture has emerged of the effects of proline analogs, including $\Delta Pro$, substituted at various loci on ACE inhibitors. At present, no rationale can be advanced to explain the diversity of observed results following substitution of $\Delta Pro$ for proline. Nevertheless, the observed results of the present invention regarding the inhibitory potency of compounds B and D make it clear that the $\Delta Pro$ moiety in the compounds disclosed herein results in novel compounds of high inhibitory potency and antihypertensive effectiveness.

EXAMPLE 1

A.

ACE activity assay

For most experiments described herein, the enzyme was assayed in 0.05M Hepes buffer, pH 8.0 containing 0.1M NaCl and 0.75M $Na_2SO_4$. The substrate employed was Benzoyl-GlyHisLeu at a final concentration of $1\times10^{-4}$M, together with about 130,000 cpm of [$^3$H]-Benzoyl GlyHisLeu (25 Ci/mmole). Enzyme was diluted in the above buffer such that 40 μl buffered enzyme was capable of hydrolyzing 13% of substrate in a 15-minute incubation at 37° C. To initiate the assay, 40 μl of enzyme and 10 μl of water or inhibitor dissolved in water were preincubated for five minutes at 37° C. Substrate, 50 μl, was then added to initiate reaction and the solution was incubated for 15 minutes at 37° C. To terminate the reaction, 1 ml of 0.1M HCl was added, following which 1 ml of ethyl acetate was added. The mixture was agitated on a rotary mixer and centrifuged brifly to separate the phases.

An aliquot, 500 μl, of the ethyl acetate layer was transferred to a liquid scintillation vial containing 10 ml of Riafluor, trademark New England Nuclear Corporation, Boston, Mass. For determination of $I_{50}$ values, enzyme activity in the presence of inhibitor at a series of different concentrations was compared to activity in the absence of inhibitor. A plot of inhibitor concentration versus percent inhibition yielded the $I_{50}$ value.

EXAMPLE 2

Preparation of N-Benzoyl-L-Phenylalanine

A mixture containing 8.21 g of L-Phenylalanine, 5.565 g of $Na_2CO_3$ in 40 ml of water and 20 ml of tetrahydrofuran (THF) was stirred at room temperature. Benzoyl chloride, 7.73 g, dissolved in 20 ml of anhydrous THF, was added gradually over a period of 45 minutes with continued stirring at room temperature. Stirring was allowed to continue for an additional hour, at which time the reaction mixture was transferred to a rotary evaporator at 30° C. to remove the THF. An excess of water was then added and the reaction mixture extracted four times with ethyl acetate. The aqueous phase was then titrated to pH 2 with 3N HCl. A white crystalline precipitate formed which was recovered by filtration, washed three times with cold dilute HCl and three times with cold water, and dried in a vacuum oven over $P_2O_5$ at about 50° C. The product was recrystallized from aqueous ethanol, yielding 8.37 g, m.p. 183° C.–184° C., which migrated at a single compound on thin layer chromatography in five separate solvent systems.

EXAMPLE 3

Preparation of N-Benzoyl-Phenylalanine-N-hydroxy-Succinimide ester 1.347 g. of Benzoyl-Phenylalanine and 0.576 g of N-hydroxy succinimide were mixed in a 1:1 (by volume) mixture of THF and dimethylformamide (DMF). The mixture was incubated at 4° C. overnight in the presence of 1.133 g of dicyclohexylcarbodiimide.

The reaction mixture was filtered and the solvent was removed under reduced pressure at 30° C. A white residue remained which was recrystallized from THF-isopropyl alcohol to yield 1.194 g (65.2%) of a white solid, m.p. 156° C.–157° C. The infrared absorption spectrum in chloroform showed bands at 3440 cm$^{-1}$ indicating an NH group, at 1818 cm$^{-1}$, 1790 cm$^{-1}$, and 1744 cm$^{-1}$, characteristic of the N-carboxy succinimide group and at 1669 cm$^{-1}$, characteristic of the N-Benzoyl moiety.

EXAMPLE 4

Synthesis of 2-benzoylphenylalanylthiopropanoic acid

A solution of benzoyl-phenylalanine prepared as in Example 2, in 30 ml of redistilled dimethylformamide (DMF) is cooled to −20° C. A solution of 1,1′-carbonyldiimidazole in 10 ml redistilled DMF is added dropwise with vigorous stirring. Temperature is not allowed to exceed −14° C. Following the addition, the solution is stirred at −10° C. for two hours. D,L-Thiolactic acid in redistilled DMF previously neutralized with redistilled N-ethylmorpholine is then added with continued stirring at −10° C. for one hour. The solution is then slowly warmed to room temperature. An approximately equal volume of ethyl acetate is added. The mixture is then cooled and neutralized with concentrated HCl in saturated NaCl. The organic phase is then washed three times with subsaturated NaCl, i.e., five volumes saturated NaCl diluted with one volume water. In some cases a three-layer system is observed. In such cases, the middle layer is saved and combined with the lower aqueous phase. The organic phase is dried over anhydrous $MgSO_4$, filtered and placed in the rotary evaporator to remove solvent. The combined aqueous phase and middle phase is acidified at 0° C. with concentrated HCl to pH 2, and extracted three times with ethyl acetate. The organic phase is washed with saturated NaCl and dried over anhydrous magnesium sulfate, filtered and rotary evaporated. A clear oil is recovered.

The resulting product, 2-benzoylphenylalanylthiopropanoic acid is useful for the synthesis of compound B. The D- and L-isomers may be resolved and then coupled to L-3,4-dehydroproline by conventional techniques. Compounds A and C may also be synthesized by the same strategy: formation of the benzoylphenylalanylthiopropanoyl derivative followed by resolution of stereoisomers where appropriate, followed by coupling to L-3,4-hydroproline.

EXAMPLE 5

Synthesis of N-(2-benzoylphenylalanylthiopropanoyl)-L-3,4-dehydroproline

Boc-L-3,4-dehydroproline (213 mg; 1 mmole) was deprotected with 1 ml of anhydrous trifluoroacetic acid for 1 hour. Anhydrous ethyl ether, ∼3 ml, was added. Solvents were removed using a rotary evaporator at 30° C. The residue was washed three times with ether and then was dried in a vacuum dessicator over NaOH.

A solution of 358 mg (1 mmole) of 2-benzoylphenylalanylthiopropanoic acid in 3 ml of redistilled DMF was cooled to −20° C. in a dry ice-acetone bath. A solution of 1,1'-carbonyldimidazole, 171 mg (1.05 mmole) in 1 ml of redistilled DMF was added dropwise, and the temperature of the reaction mixture was maintained at −10° C. to −15° C. The reaction mixture was stirred for two hours. A cold solution of L-3,4-dehydroproline trifluoroacetate in 2 ml of DMF (neutralized with triethylamine) was added. The reaction mixture was warmed slowly to room temperature. Solvent was removed by rotary evaporation, using high vacuum, at 35° C. The residue was dissolved in 10 ml of ethyl acetate and 2 ml of H₂O. The mixture was acidified with 1N HCl to pH 2 at 0° C. and was mixed. The organic phase was separated and saved. The aqueous phase was extracted three more times with 5 ml of ethyl acetate.

The combined organic phase was washed twice with H₂O, three times with saturated NaCl and then was decolorized with charcoal. The organic phase was dried with anhydrous MgSO₄ and then filtered. The filtrate was evaporated to dryness on a rotary evaporator, and an oily product, 366 mg, was obtained. The product was purified by chromatography on Sephadex LH-20 (1.2×98 cm) equilibrated and eluted with methanol. Fractions of 150 drops (2.9 ml) were collected. The desired compound was eluted in fractions 24–29. Solvent was removed by rotary evaporation.

Additional purification was achieved by a second chromatography step on Sephadex LH-20. The second column was equilibrated and eluted with isopropanol, peak fractions were pooled and solvent was removed by rotary evaporation. The product was approximately 95% pure as judged by thin layer chromatography in two solvent systems: benzene:acetic acid:water, 9:9:1 (part by volume), and n-butanol:acetic acid:water, 150:26:24 (parts by volume).

EXAMPLE 6

Preparation of 2-thiolpropanoyl-L-3,4-dehydroproline

Two mg of N-(2-benzoylphenylalanylthiopropanoyl)-L-3,4-dehydroproline, prepared as described in Example 5, was hydrolyzed with 0.5 ml of 5.5N NH₃ in methanol for 30 minutes at room temperature. NH₃ and methanol were removed by a stream of dry N₂. One mole equivalent of D,L-dithiothreitol was added before assay.

The reaction products were separated by chromatography on Sephadex LH-20, eluted with isopropanol as described in Example 5.

EXAMPLE 7

Synthesis of compound B: N-(2-benzoylphenylalanylthiopropanoyl)-L-3,4-dehydroproline A reaction mixture containing 2-thiopropanoyl-L-3,4-dehydroproline, prepared as described in Example 6, 1-hydroxybenzotriazole (HOBt), and N-benzoylphenylalanyl-N-hydroxy-succinimide ester, prepared as described in Example 3, is cooled in an ice bath at approximately 0° C., after which N-ethylmorpholine is added. The reaction mixture is stirred in an ice bath for three hours, incubated at 4° C. overnight, then at room temperature for 20 hours. The reaction is terminated by the addition of N,N-dimethyl-1,3-propanediamine, and stirred for an additional two hours. Ethyl acetate is added to the reaction mixture which is then washed by extraction with cold 0.1N HCl, followed by two washes with water and three washes with saturated NaCl. The mixture is then dried over anhydrous MgSO₄ and filtered. The solvent is removed under reduced pressure in a rotary evaporator, yielding a clear, oily product.

The product is purified by chromatography on Sephadex LH-20, eluted with THF. Re-chromatography of side fractions may yield additional product. Peak fractions are pooled and the solvent removed under high vacuum. The product is washed with ether, then dissolved in THF, transferred to a vial, dried in the stream of nitrogen, then further dried over P₂O₅ overnight.

EXAMPLE 8

Synthesis of compound A: N-[3-(benzoylphenylalanylthio)-2-D-methylpropanoyl]-L-3,4-dehydroproline Compound A is synthesized essentially by the method of Example 5, by coupling L-3,4-dehydroproline to 3-(benzoylphenylalanylthio)-2-D-methylpropanoic acid using 1,1'-carbonylidimidazole.

Compound A is alternatively synthesized essentially by the method of Example 7, starting from 3-thio-2-D-methylpropanoyl-L-3,4-dehydroproline and N-benzoylphenylalanyl-N-hydroxy-succinimide ester.

EXAMPLE 9

Synthesis of compound C: N-(3-benzoylphenylalanylthiopropanoyl)-L-3,4-dehydroproline Compound C is synthesized essentially by the method of Example 5, by coupling L-3,4-dehydroproline to 3-benzoylphenylalanylthiopropanoic acid using 1,1'-carbonyldiimidazole.

Compound C is alternatively synthesized essentially by the method of Example 7, starting from 3-thiopropanoyl-L-3,4-dehydroproline and N-benzoylphenylalanyl-N-hydroxy-succinimide ester.

EXAMPLE 10

The inhibitory potency of N-(2-benzoylphenylalanylthiopropanoyl)-L-3,4-dehydroproline (B) in vitro was measured in the assay system described in Example 1. The enzyme preparation was ACE purified from human urine as described by Ryan, J. W., et al, *Tissue and Cell* 10, 555 (1978). The result is shown in the Table.

TABLE

| Compound | $I_{50}$ |
| --- | --- |
| B (racemic) | $3 \times 10^{-9}$ M |

EXAMPLE 11

Oral effectiveness of compound (B)

Rats (210–290 g body weight) were fasted overnight and then anesthetized with intraperitoneal pentobarbital, 50–60 mg/kg. Tracheostomy was performed and the animals were ventilated mechanically. A cannula was inserted into a femoral vein for injection of angiotensin I or II, and a second cannula was inserted into a common carotid artery for direct measurement of arterial blood pressure. Heparin, 1,000 units, was injected via the femoral vein to prevent coagulation. Blood pressure was measured with a pressure transducer connected to a polygraph. The rats were injected with 160 ng of angiotensin I or 80 ng of angiotensin II in 20 μl of 0.9 g % NaCl; an amount of angiotensin I or II sufficient to raise mean arterial blood pressure by 27–40 mm Hg. After the responsiveness of a given rat to angiotensins I and II was established, compound (B) at 10 mg (drug dissolved in 0.5 ml of H$_2$O plus 10 μl of 1N NaHCO$_3$), was given via a stomach tube. At timed intervals, the effects of 160 ng of angiotensin I or 80 ng of angiotensin II on mean arterial blood pressure were tested. Results are shown below:

| Oral effectiveness of N—(2-benzoylphenylalanylthiopropanoyl)-L-3,4-dehydroproline (B). | |
| --- | --- |
| Time After Oral Administration (Minutes) | Blood Pressure Response to 160 mg of Angiotensin I Drug at 10 mg |
| −5 | 100% (27 mmHg) |
| +3 | 100 |
| 9 | 81 |
| 14 | 74 |
| 24 | 74 |
| 28 | 74 |
| 34 | 63 |
| 44 | 56 |
| 54 | 44 |
| 64 | 56 |
| 85 | 37 |
| 94 | 44 |
| 104 | 74 |
| 114 | 56 |
| 146 | 100% |

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth, and as follows in the scope of the appended claims.

We claim:

1. An angiotensin converting enzyme inhibitor selected from the group consisting of: N-[3-(benzoylphenylalanylthio)-2-D-methylpropanoyl]-L-3,4-dehydroproline, N-(2-benzoylphenylalanylthiopropanoyl)-L-3,4-dehydroproline, and N-(3-benzoylphenylalanylthiopropanoyl)-L-3,4-dehydroproline.

2. The compound N-[3-(benzoylphenylalanylthio)-2-D-methylpropanoyl]-L-3,4-dehydroproline.

3. The compound N-(2-benzoylphenylalanylthiopropanoyl)-L-3,4-dehydroproline.

4. The compound N-(3-benzoylphenylalanylthiopropanoyl)-L-3,4-dehydroproline.

5. A method for inhibiting angiotensin converting enzyme in vivo comprising administering orally an effective dose of an inhibitor selected from the group consisting of: N-[3-(benzoylphenylalanylthio)-2-D-methylpropanoyl]-L-3,4-dehydroproline, N-(2-benzoylphenylalanylthiopropanoyl)-L-3,4-dehydroproline, and N-(3-benzoylphenylalanylthiopropanoyl)-L-3,4-dehydroproline.

6. The method of claim 5 wherein the inhibitor is N-[3-(benzoylphenylalanylthio)-2-D-methylpropanoyl]-L-3,4-dehydroproline.

7. The method of claim 5 wherein the inhibitor is N-(2-benzoylphenylalanylthiopropanoyl)-L-3,4-dehydroproline.

8. The method of claim 5 wherein the inhibitor is N-(3-benzoylphenylalanylthiopropanoyl)-L-3,4-dehydroproline.

9. A method for reducing blood pressure in vivo comprising administering orally an effective dose of a compound selected from the group consisting of: N-[3-(benzoylphenylalanylthio)-2-D-methylpropanoyl]-L-3,4-dehydroproline, N-(2-benzoylphenylalanylthiopropanoyl)-L-3,4-dehydroproline, and N-(3-benzoylphenylalanylthiopropanoyl)-L-3,4-dehydroproline.

10. The method of claim 9 wherein the compound is N-[3-(benzoylphenylalanylthio)-2-D-methylpropanoyl]-L-3,4-dehydroproline.

11. The method of claim 9 wherein the compound is N-(2-benzoylphenylalanylthiopropanoyl)-L-3,4-dehydroproline.

12. The method of claim 9 wherein the compound is N-(3-benzoylphenylalanylthiopropanoyl)-L-3,4-dehydroproline.

13. A composition comprising an orally effective dose of the angiotensin converting enzyme inhibitor of claim 1, and a physiologically acceptable vehicle therefor.

* * * * *

UNITED STATES PATENT AND TRADEMARK OFFICE
CERTIFICATE OF CORRECTION

PATENT NO. : 4,707,490
DATED : November 17, 1987
INVENTOR(S) : James W. Ryan and Alfred Chung It is certified that error appears in the above-identified patent and that said Letters Patent is hereby corrected as shown below:

Col 2, line 45, "lovel" should read "level"

Col 4, line 9, delete the space after "1__-4x10$^{-8}$M" so that it reads "1-4x10$^{-8}$M"

Col 7, lines 67, add "s" to "(part__ by volume)" so that it reads "(parts by volume)"

Col 9, line 45 "160mg" should read "160ng

Signed and Sealed this

Twentieth Day of September, 1988

Attest:

DONALD J. QUIGG

Attesting Officer

Commissioner of Patents and Trademarks